(12) United States Patent
Jeon et al.

(10) Patent No.: US 9,128,040 B2
(45) Date of Patent: Sep. 8, 2015

(54) NANOPORE DEVICE, METHOD OF FABRICATING THE SAME, AND DNA DETECTION APPARATUS INCLUDING THE SAME

(75) Inventors: Tae-han Jeon, Hwaseong-si (KR); Jeo-young Shim, Yongin-si (KR); Kun-sun Eom, Seoul (KR); Dong-ho Lee, Seongnam-si (KR); Hee-jeong Jeong, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 449 days.

(21) Appl. No.: 13/572,516

(22) Filed: Aug. 10, 2012

(65) Prior Publication Data
US 2013/0161194 A1    Jun. 27, 2013

(30) Foreign Application Priority Data
Dec. 26, 2011    (KR) .................. 10-2011-0142388

(51) Int. Cl.
| | | |
|---|---|---|
| *G01N 27/327* | (2006.01) | |
| *C23C 14/34* | (2006.01) | |
| *G01N 33/487* | (2006.01) | |
| *B82Y 30/00* | (2011.01) | |
| *B82Y 40/00* | (2011.01) | |
| *B82Y 15/00* | (2011.01) | |

(52) U.S. Cl.
CPC ............ *G01N 27/3278* (2013.01); *C23C 14/34* (2013.01); *G01N 33/48721* (2013.01); *B82Y 15/00* (2013.01); *B82Y 30/00* (2013.01); *B82Y 40/00* (2013.01)

(58) Field of Classification Search
CPC .................... G01N 27/3278; G01N 33/48721; B82Y 15/00; B82Y 30/00; B82Y 40/00
USPC .......... 204/455, 601–605; 977/780–781, 880, 977/940, 924
See application file for complete search history.

(56) References Cited

U.S. PATENT DOCUMENTS

| | | | |
|---|---|---|---|
| 6,015,714 | A | 1/2000 | Baldarelli et al. |
| 6,362,002 | B1 | 3/2002 | Denison et al. |
| 6,428,959 | B1 | 8/2002 | Deamer |
| 8,003,319 | B2 | 8/2011 | Polonsky et al. |
| 2006/0275778 | A1* | 12/2006 | Wu et al. ............... 435/6 |
| 2011/0155574 | A1 | 6/2011 | Golovchenko et al. |

FOREIGN PATENT DOCUMENTS

| | | |
|---|---|---|
| EP | 2014761 A1 | 1/2009 |
| KR | 10-0730350 B1 | 6/2007 |

OTHER PUBLICATIONS

Liang et al., "Nanogap Detector Inside Nanfluidic Channel for Fast Real-Time Label-Free DNA Analysis," *Nano Letters*, 2008, 8-5: 1472-1476.

(Continued)

*Primary Examiner* — J. Christopher Ball
(74) *Attorney, Agent, or Firm* — Leydig, Voit & Mayer, Ltd.

(57) ABSTRACT

A nanopore device including a nanopore formed by penetrating a thin layer, a nanochannel formed at an entrance of the nanopore, and a filler in the nanochannel, as well as a method of fabricating the nanopore device and an apparatus including the nanopore device.

26 Claims, 5 Drawing Sheets

(56) References Cited

OTHER PUBLICATIONS

Jo, Kyubong et al., "Nanochannel confinement: DNA stretch approaching full contour length," *Lab Chip*, 11, 1721-1729 (2011).

Lu, Bo et al., "Origins and Consequences of Velocity Fluctuations during DNA Passage through a Nanopore," *Biophysical Journal*, 101, 70-79 (2011).

\* cited by examiner

NANOPORE DEVICE, METHOD OF FABRICATING THE SAME, AND DNA DETECTION APPARATUS INCLUDING THE SAME

CROSS-REFERENCE TO RELATED APPLICATIONS

This application claims the benefit of Korean Patent Application No. 10-2011-0142388, filed on Dec. 26, 2011, in the Korean Intellectual Property Office, the disclosure of which is incorporated herein in its entirety by reference.

BACKGROUND

1. Field

The present disclosure relates to a nanopore device, a method of fabricating the same, and a DNA detection apparatus including the same, and more particularly, to a nanopore device that is capable of controlling a translocation speed of DNAs which translocate through a nanopore, methods of fabricating the same, and a DNA detection apparatus including the same.

2. Description of the Related Art

A variety of methods for detecting target biomolecules in a sample have been developed. Among these methods, a nanopore method has been used in conjunction with a nucleic acid (DNA) detection system with high-sensitivity. A nanopore DNA detection apparatus may detect DNA from a slight change in current which occurs during electrophoresis when DNA translocates through a nanopore formed in a thin layer.

However, the DNA detection accuracy is low because the DNA translocation speed is very high. For example, the speed of DNA translocating through a nanopore is about $10^6$ to $10^7$ bp/sec (bp represents "base pair") in conventional systems. That is, since it takes only about 100 nsec for one strand of DNA to translocate through a nanopore, a high performance measuring instrument having a bandwidth of about 10 to 100 MHz is necessary to measure a slight change (~1 nA) in current which occurs when DNA translocates through a nanopore. This makes it difficult to miniaturize a DNA detection device and reduce manufacturing costs. Additionally, it causes measurement errors.

Also, DNA is generally present in a state where a very long strand is twisted in a complicated form, and DNA twisting may be randomly different in each DNA molecule. Therefore, the time it takes for DNA to enter a nanopore, and the translocation speed in the nanopore, may differ according to the nature of DNA twisting at the moment when the DNA enters into the nanopore. This is an important factor that affects the accuracy of DNA detection.

SUMMARY

Provided is a nanopore device which may control a DNA translocation speed passing through a nanopore and methods of fabricating the nanopore device.

Provided is a nucleic acid detection apparatus including the nanopore device, the apparatus having improved DNA detection accuracy.

Additional aspects will be set forth in part in the description which follows and, in part, will be apparent from the description, or may be learned by practice of the presented embodiments.

According to an aspect of the present invention, a nanopore device may include a nanopore having a diameter in a nanoscale range; a nanochannel, which may be formed to be connected to an entrance of the nanopore and may have a diameter larger than the diameter of the nanopore; and a filler filled in the nanochannel.

The filler may be a material that allows DNA to pass through the nanopore with a translocation speed that is reduced as compared to the translocation speed of DNA through the nanopore without a filler. The filler may be, for instance, at least one of a silica gel, an agarose gel, and a poly acrylamide gel.

The filler may be a porous material layer comprising at least one of a porous zeolite and a porous anodized aluminum oxide (AAO).

The nanochannel may be formed along the same axis with the nanopore to extend from the nanopore so that a moving direction of target biomolecules in the nanochannel may be the same as a translocating direction of the target biomolecules in the nanopore.

The nanopore device may include a substrate; a nanopore layer that may be formed on the substrate and comprises the nanopore; and a nanochannel layer that may be formed on the nanopore layer and comprises the nanochannel.

The nanopore device may further include an opening formed by penetrating the substrate exposing a part of a lower surface of the nanopore layer, wherein the nanopore may be formed by penetrating a partial region of the nanopore layer exposed by the opening.

The nanochannel perpendicularly may penetrate the nanochannel layer and may be formed along the same axis with the nanopore.

The opening may have a conical surface which becomes narrower toward an entrance.

The nanopore and the nanochannel may be formed perpendicular to each other so that a moving direction of target biomolecules in the nanochannel and a translocating direction of the target biomolecules in the nanopore may be perpendicular to each other.

The nanopore divide may include an inlet connected to the nanochannel, wherein a sample may enter into the nanochannel through the inlet.

For example, the inlet may be placed on an upper surface of each end of the nanochannel, and the nanopore may be formed at the center of a lower surface of the nanochannel.

Otherwise, the inlet may be formed in an upper area at a first end of the nanochannel, and the nanopore may be formed in a lower area at a second end which may be located at an opposite side of the first end of the nanochannel.

The nanopore device may further include an opening formed by penetrating the substrate exposing a part of the lower surface of the nanopore layer, wherein the nanopore may be formed by penetrating a partial region of the nanopore layer posed by the opening.

The nanochannel may be formed between the nanopore layer and the cover layer by partially removing the nanochannel.

The inlet may be formed by penetrating a partial region of the cover layer corresponding to the nanochannel.

According to another aspect of the present invention, a nucleic acid detection apparatus may include the nanopore device described above; a reservoir for containing the sample that translocated through the nanopore; and a power supply to form an electric field around the nanopore in order to move the target biomolecules in the sample.

According to another aspect of the present invention, a method of fabricating a nanopore device may include forming a nanopore layer on an upper surface of a substrate and patterning a lower surface of the substrate by using a mask; forming a nanochannel layer on the nanopore layer; forming an opening in the substrate by etching the substrate until a lower surface of the nanopore layer is partially exposed; forming a nanochannel by partially removing the nanochannel layer until an upper surface of the nanopore layer is partially exposed; forming a nanopore which penetrates the nanopore layer by puncturing a partial region of the nanopore layer where both upper and lower surfaces are exposed; and filling a filler in the nanochannel.

The method may further include forming a cover layer on the nanochannel layer in order to cover the nanochannel and the nanopore.

The method may further include forming an inlet by penetrating a partial region of the cover layer corresponding to the nanochannel.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
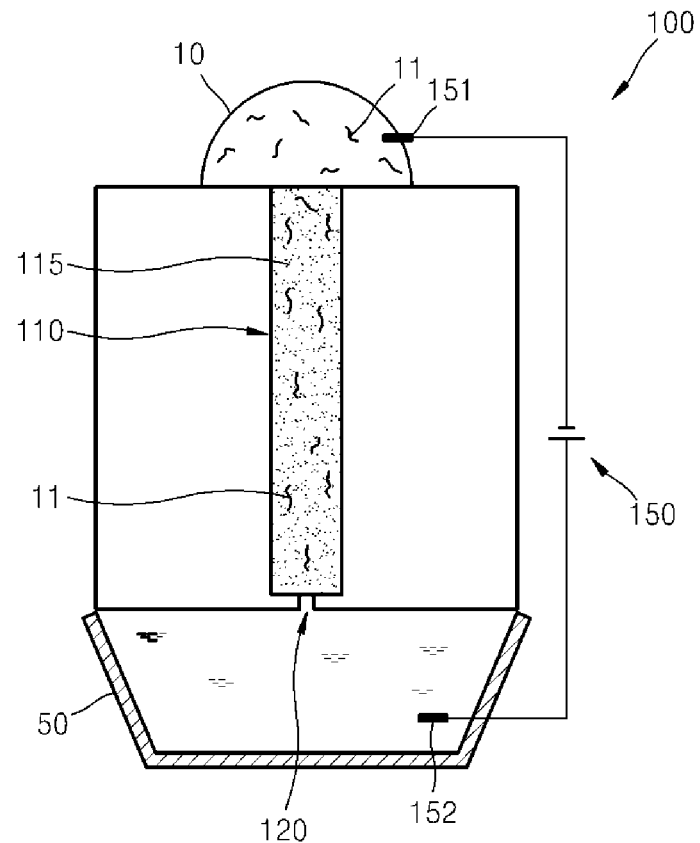
FIG. 1 is a conceptual view schematically illustrating a structure and operation of a nanopore device and a DNA detection apparatus including the nanopore device according to an embodiment.

Hereinafter, reference will now be made in detail to embodiments of a nanopore device, a method of fabricating the same, and a DNA detection apparatus including the same, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

FIG. 1 is a conceptual view schematically illustrating a structure and operation of a nanopore device and a DNA detection apparatus including the nanopore device according to an embodiment.

Referring to FIG. 1, a nanopore device 100 may include a nanopore 120 having a fine diameter in a nanoscale range, a nanochannel 110, which may be formed to be connected to an entrance of the nanopore 120, has a diameter larger than the diameter of the nanopore 120, and a filler 115 filled in the nanochannel 110.

The nanopore may have a diameter in the nanoscale range (e.g., about 1000 nm or less, or about 500 nm or less, such as about 100 nm or less, or about 50 nm or less, or even about 20 nm or less or 10 nm or less). For example, a diameter of the nanopore 120 may be about 100 nm or less, preferably about 10 nm or less, especially about 5 nm, a diameter of the nanochannel 110 may be about 50 nm to about 500 nm, and a length of the nanochannel 110 may be in a range of about 50 nm to about 100 um. Also, a length of the nanopore 120 may be 100 nm or less. For example, the length of the nanopore may be about 30 nm. As shown in FIG. 1, the nanochannel 110 is formed along the same axis with the nanopore 120 and may be formed to extend from the nanopore 120. In such structure, a moving direction of target biomolecules such as DNA in the nanochannel 110 is the same as a direction the target biomolecules translocate through the nanopore 120.

The filler 115 serves to reduce a movement speed of the target biomolecules in the nanochannel 110. Also, the filler 115 serves to open up a plurality of the target biomolecules, such as DNA, which are randomly twisted in various shapes to a regular straight type while the target biomolecules are moving inside the filler 115. The filler can be a material different from the material of the substrate comprising the nanopore (i.e., the material in which the nanopore is formed). For instance, the filler 115 may be a gel so that mechanical friction occurs when the target biomolecules pass through the gel. For example, a silica gel, an agarose gel, or a poly acrylamide gel may be used as the filler 115.

Moreover, a DNA detection apparatus according to an embodiment shown in FIG. 1 may include the nanopore device 100, a reservoir 50 for containing a sample translocated through the nanopore 120, and a power supply 150 forming an electric field around the nanopore 120 in order to move the target biomolecules in the sample. As shown in FIG. 1, the power supply 150 may include a first electrode 151 disposed in a droplet 10 of the sample provided at an entrance of the nanochannel 110 of the nanopore device 100, and a second electrode 152 disposed in the reservoir 50. Although not shown in FIG. 1, the power supply 150 may further include a detection apparatus to detect a change in a current generated when the target biomolecules translocate through the nanopore 120.

Hereinafter, operation of the nanopore device 100 and the DNA detection apparatus including the nanopore device 100 described above will be explained. First, an electrically conductive solution, for example KCl solution, is filled in the nanochannel 110 and the reservoir 50 allowing a current to flow from the nanochannel 110 to the reservoir 50. Also, the droplet 10 of the sample, in which target biomolecules 11 to be detected are dispersed, is provided at the entrance of the nanochannel 110 of the nanopore device 100. Then, when a prescribed voltage is applied to the droplet 10 and the reservoir 50 from the power supply 150, a plurality of the target biomolecules 11 in the droplet 10 move along the electric field formed between the droplet 10 and the reservoir 50. That is, the target biomolecules 11 move from the droplet 10 to the nanopore 120 via the nanochannel 110.

The target biomolecules 11 that arrived at the nanopore 120 sequentially translocate through the nanopore 120. Then, presence of the target biomolecules 11 may be determined by detecting a change in a current generated when the target biomolecules translocate through the narrow nanopore 120. However, if the target biomolecules 11 translocate through the nanopore 120 too fast, an accurate detection/analysis may be difficult. According to the present embodiment, the movement speed of the target biomolecules 11 may be suppressed because the nanochannel 110 is filled with the filler 115. Also, according to the present embodiment, since the electric field may be homogenously dispersed in the nanochannel 110 and the nanopore 120 rather than being intensely concentrated on the nanopore 120, an increase in the movement speed of the target biomolecules 11 due to a strong electric field around the nanopore 120 may be prevented, and the target biomolecules 11 may move from the nanochannel 110 to the nanopore 120 at a regular speed. In addition, the target biomolecules 11, such as DNA, may be straightened to one strand while translocating through the filler 115 inside the nanochannel 110. Therefore, each of the target biomolecules 11 that arrived at the nanopore 120 may translocate through the nanopore 120 in a regular shape. As a result, a time for the plurality of the target biomolecules 11 to enter the nanopore 120 and the moving speed of the target biomolecules 11 in the nanopore 120 may be maintained regularly, and a measurement of the target biomolecules 11 may be consistently and accurately performed.

Figure 2:
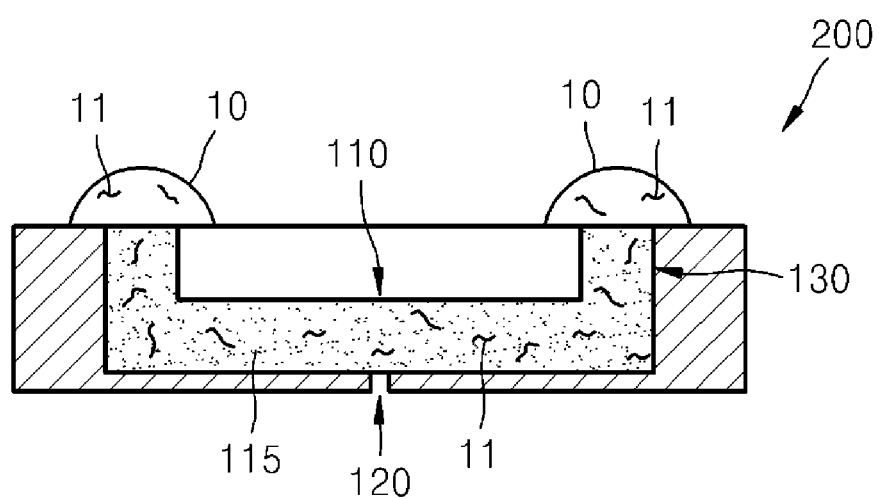
FIG. 2 is a conceptual view schematically illustrating a structure of a nanopore device according to an embodiment.

In a case of the nanopore device 100 shown in FIG. 1, an axis direction of the nanochannel 110 and an axis direction of the nanopore 120 are the same. Thus, a direction of the target biomolecules 11 moving in the nanochannel 110 is the same as a direction the target biomolecules 11 translocate through the nanopore 120. However, the nanochannel 110 and the nanopore 120 may be perpendicular to each other. FIG. 2 is a conceptual view schematically illustrating a structure of a nanopore device according to another embodiment of which the nanochannel 110 and the nanopore 120 are perpendicular.

Referring to FIG. 2, a nanopore device 200 may include a nanopore 120 which has a fine diameter in nanoscale range and is formed in a vertical direction, a nanochannel 110 which may be formed to be connected to an entrance in a horizontal direction and has a diameter larger than the diameter of the nanopore 120, a filler 115 filled in the nanochannel 110, and an inlet 130 which is connected to the nanochannel 110.

As shown in FIG. 2, since the nanopore 120 is formed in a vertical direction, and the nanochannel 110 is formed in a horizontal direction, an axis of the nanochannel 110 and an axis of the nanopore 120 are perpendicular to each other. Thus, a direction of target biomolecules 11 moving in the nanochannel 110 and a direction the target biomolecules 11 are translocated through the nanopore 120 are perpendicular to each other. That is, the target biomolecules 11 first move in a horizontal direction along with the nanochannel 110, and then translocate through the nanopore 120 in a vertical direction. The inlet 130 which provides the target biomolecules 11 in a droplet 10 to the nanochannel 110 may also be formed perpendicular to the nanochannel 110 like the nanopore 120.

Figure 3:
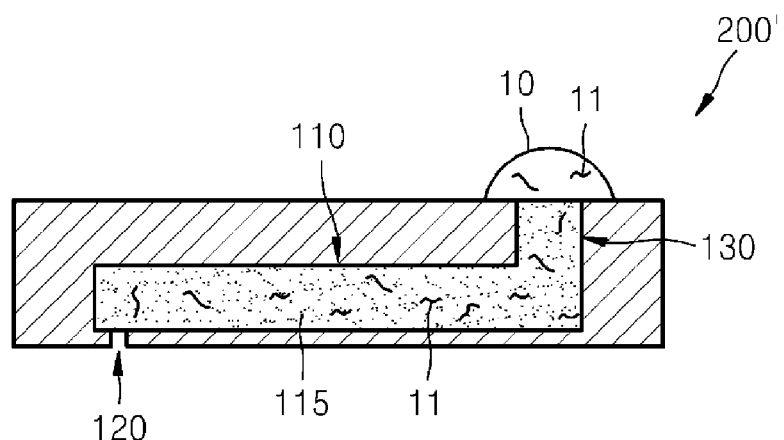
FIG. 3 is a conceptual view schematically illustrating a structure of a nanopore device according to an embodiment.

Also, in an embodiment of FIG. 2, the inlet 130 formed on both sides of the nanochannel 110 and the nanopore 120 formed under the middle of the nanochannel 110 are only an example. Relative positions of the inlet 130 and the nanopore 120 in regard to the nanochannel 110 may be selected according to a purpose of the device. For example, in the case of a nanopore device 200' illustrated in FIG. 3, one inlet 130 may be formed in an upper area at one end of a nanochannel 110, and one nanopore 120 may be formed in a lower area at the other end of the nanochannel 110.

FIGS. 4A through 4G are cross-sectional views illustrating a method of fabricating the nanopore device 200 shown in FIG. 2 in detail. Hereinafter, the method of fabricating the nanopore device 200 is explained in reference to FIGS. 4A through 4G.

Figure 4A:
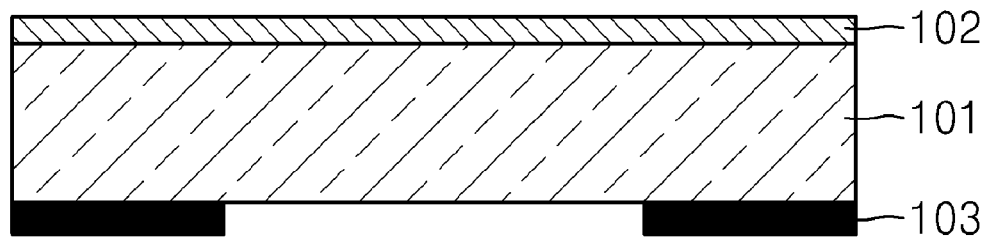
FIGS. 4A through 4G are cross-sectional views illustrating a method of fabricating the nanopore device shown in FIG. 2.

First, as shown in FIG. 4A, a nanopore layer 102, wherein a nanopore 120 will be formed later, is formed on an upper surface of a substrate 101. A mask 103 is formed and patterned on a lower surface of the substrate 101. The substrate 101 may be formed of, for example, silicon (Si), and a thickness of the substrate 101 may be, for example, about 300 um. Also, the nanopore layer 102 may be formed of, for example, silicon nitride (SiNx), and a thickness of the nanopore layer 102 may be, for example, about 20 nm. The mask 103 may also be formed of silicon nitride (SiNx), and a thickness of the mask 103 may be, for example, about 20 nm. The mask 103 is for forming an opening 105 (see FIG. 4C) on the substrate 101. Thus, the central region of the mask 103 where the opening 105 is to be formed is removed by patterning, and thus, the mask 103 may only be formed on a portion of the lower surface of the substrate 101.

Figure 4B:
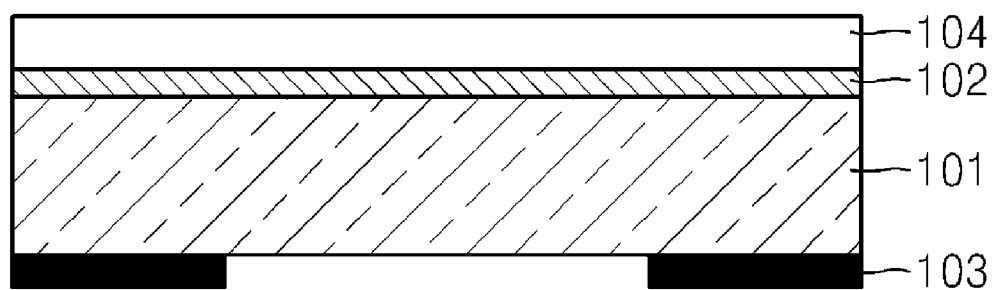

Next, as shown in FIG. 4B, a nanochannel layer 104 wherein a nanochannel 110 will be formed later is formed on an upper surface of the nanopore layer 102. The nanochannel layer 104 may be formed of silicon oxide ($SiO_2$), and a thickness of the nanochannel layer 104 may be about 100 nm. However, the nanochannel layer 104 may be formed by using silicon nitride, which is a material used in the nanopore layer 102 instead of silicon oxide. The nanopore layer 102 and the nanochannel layer 104 may be flatly formed on the substrate 101.

Figure 4C:
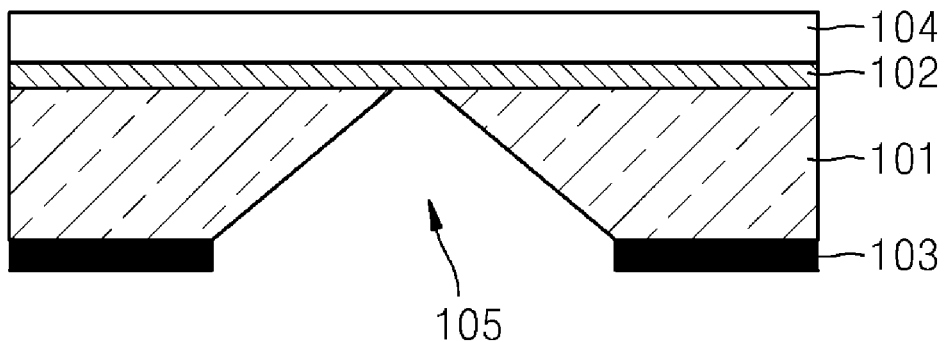

Thereafter, referring FIG. 4C, the substrate 101 is etched from a lower surface of the substrate 101 until a lower surface of the nanopore layer 102 on the upper surface of the substrate 101 is exposed. Then, the opening 105 penetrating a center of the substrate 101 may be formed, and the nanopore layer 102 may be exposed under the substrate 101 by the opening 105. As shown in FIG. 4C, the opening 105 has a conical surface. Thus, only a partial narrow region of the lower surface of the nanopore layer 102 may be exposed under the substrate 101.

Figure 4D:
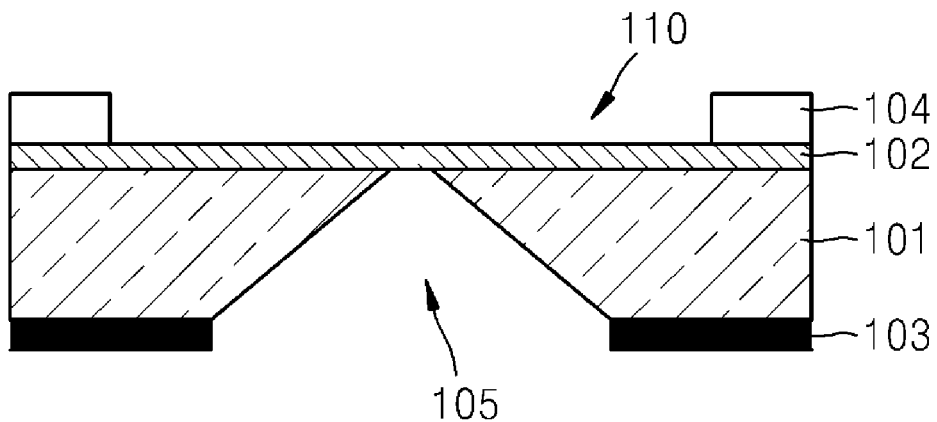

In addition, as shown in FIG. 4D, the nanochannel 110 is formed by partially removing the nanochannel layer 104. As the nanochannel 110 is formed by removing the nanochannel layer 104, the upper surface of the nanopore layer 102 may be exposed through the nanochannel 110. Thus, both the upper surface and the lower surface of the nanopore layer 102 may be exposed at its center. The exposed upper surface of the nanopore layer 102 may be a bottom surface of the nanochannel 110. Removal of the nanochannel layer 104 may be performed using, for example, a focused ion beam (FIB) milling technique.

Figure 4E:
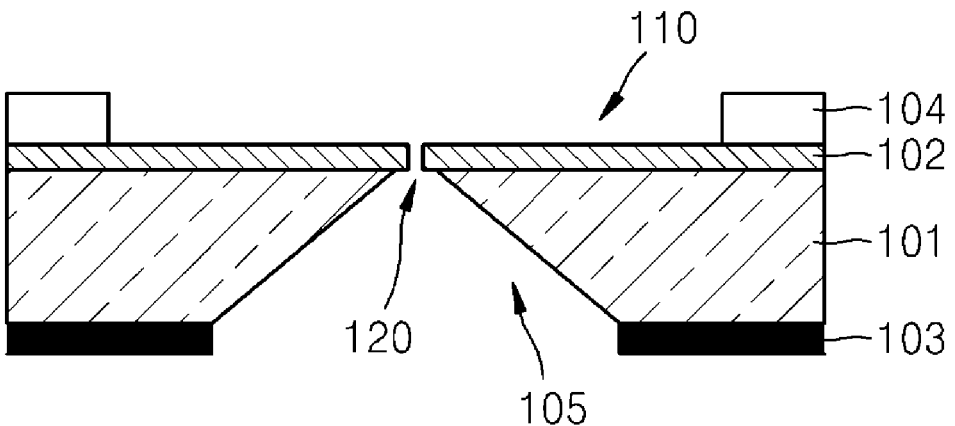

Next, as shown in FIG. 4E, the nanopore 120 penetrating the nanopore layer 102 may be formed by puncturing a partial region of the center of the nanopore layer 102, of which both the upper and lower surfaces are exposed. The nanopore 120 may be fabricated using transmission electron microscope (TEM) equipment.

Figure 4F:
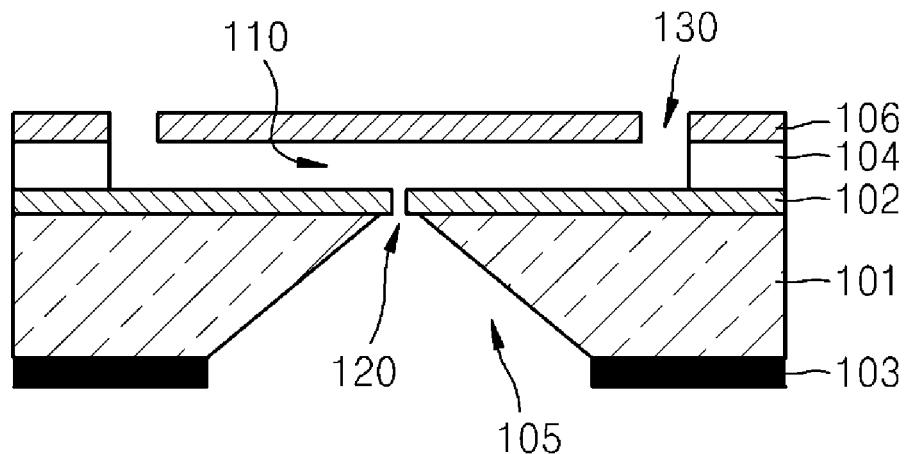
Figure 4G:
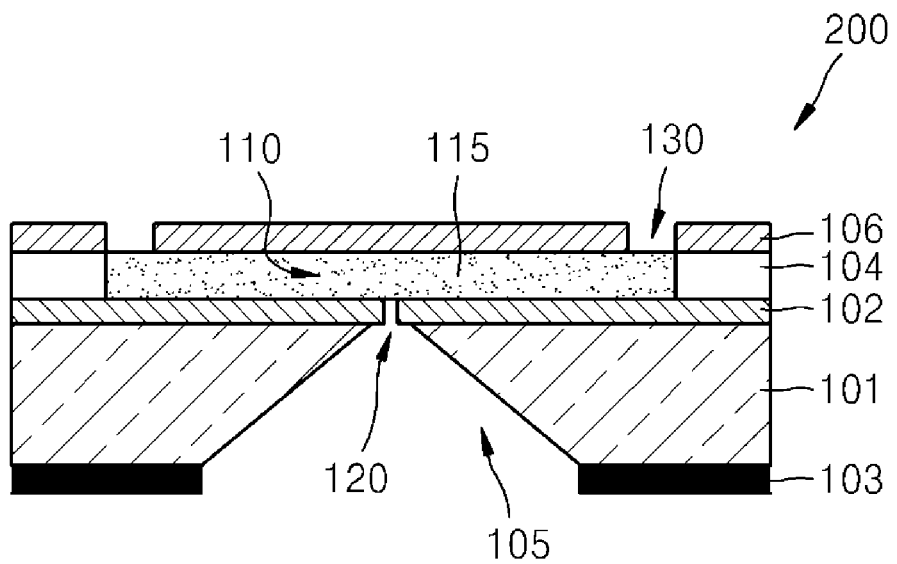

After the nanochannel 110 and the nanopore 120 are formed, as shown in FIG. 4F, a cover layer 106 to cover both of the nanochannel 110 and the nanopore 120 is formed on the upper surface of the nanochannel layer 104. Thus, the nanochannel 110 may be formed between the cover layer 106 and the nanopore layer 102. Also, an inlet 130 may be formed by penetrating partial regions of the cover layer 106 corresponding to both ends of the nanochannel 110. The cover layer 106 may be formed of a polymer material, for example, polymethylmethacrylate (PMMA). Lastly, as shown in FIG. 4G, a nanopore device 200 may be completed by filling the nanochannel 110 with a gel-type filler 115 through the inlet 130. As described above, a silica gel, an agarose gel, or a poly acrylamide gel may be used as the filler 115.

Figure 5:
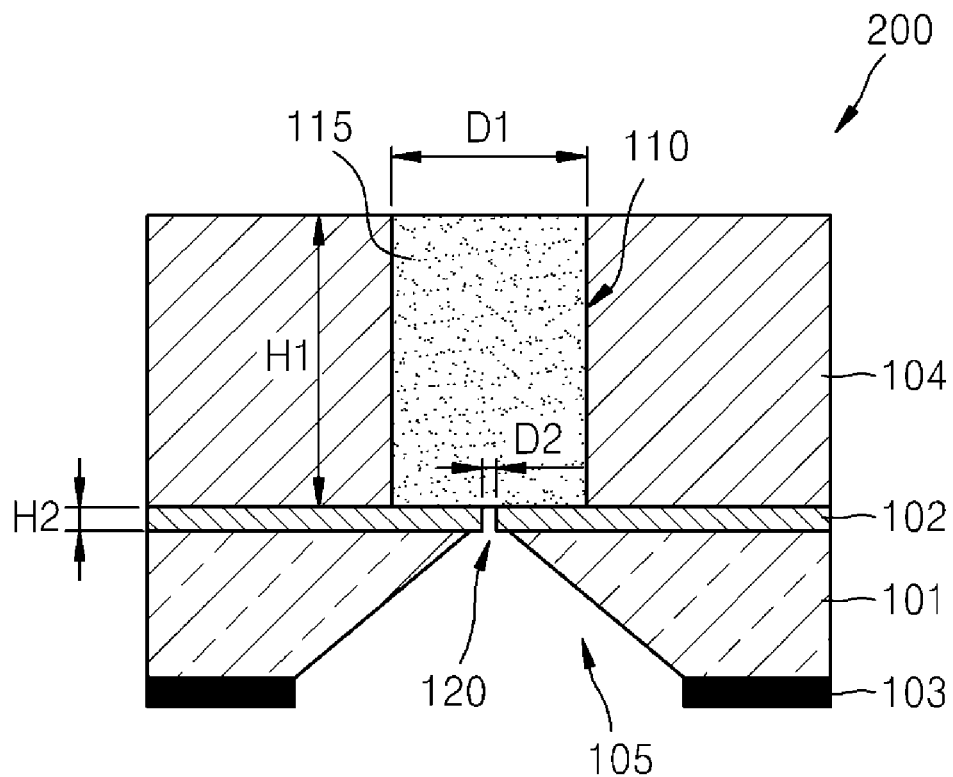
FIG. 5 is a cross-sectional diagram schematically illustrating a structure of the nanopore device shown in FIG. 1.

A method of fabricating the nanopore device 200 shown in FIG. 2 has been described above. However, the nanopore device 100 shown in FIG. 1 may also be fabricated by using the same method described above. FIG. 5 is a cross-sectional diagram schematically illustrating a structure of the nanopore device 100 in FIG. 1 manufactured by the method described above.

Referring to FIG. 5, the nanopore device 100 may include a substrate 101, a nanopore layer 102 that is formed on the substrate 101 and includes a nanopore 120, and a nanochannel layer 104 that is formed on the nanopore layer 102 and includes a nanochannel 110. An opening 105 is formed in the substrate 101 to partially expose the lower surface of the nanopore layer 102. The opening 105 has an inclined conical surface which becomes broader toward an entrance of the opening 105. Thus, only a narrow partial region of the nanopore layer 102 may be exposed under the substrate 101. The nanopore 120 is formed by penetrating a partial region of the nanopore layer 102 exposed by the opening 105. Also, the nanochannel 110 is formed by penetrating the nanochannel layer 104. The nanochannel 110 may be formed vertically along the same axis with the nanopore 120. A gel-type filler 115 is filled in the nanochannel 110. In the nanopore device 100 shown in FIG. 5, a diameter D1 of the nanochannel 110 may be, for example, in a range from about 50 nm to about 500 nm, and a thickness H1 of the nanochannel layer 104 may be in a range from about 50 nm to about 100 um. Also, a diameter D2 of the nanopore 120 may be, for example, about 5 nm, and a thickness H2 of the nanopore layer 102 may be about 20 nm.

Figure 6:
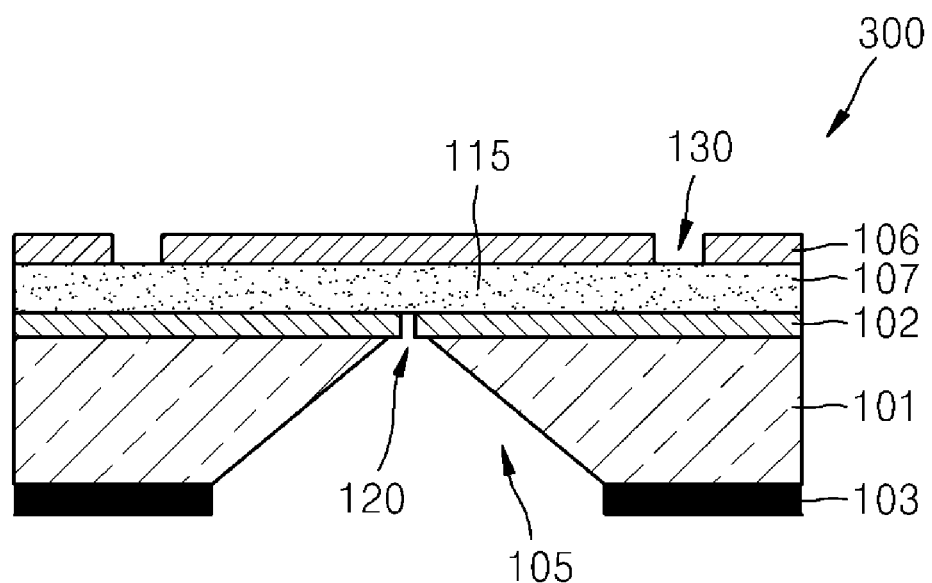
FIG. 6 is a cross-sectional view schematically illustrating a structure of a nanopore device according to an embodiment.

Meanwhile, a porous material having a plurality of pores in a nanoscale range may be used instead of the gel-type filler 115 mentioned above. FIG. 6 is a cross-sectional view schematically illustrating a structure of a nanopore device using a porous material according to another embodiment.

Referring to FIG. 6, a nanopore device 300 may include a substrate 101, a nanopore layer 102 formed on the substrate 101, a porous material layer 107 formed on the nanopore layer 102, and a cover layer 106 formed on the porous material layer 107. As described above, an opening 105 is formed exposing a lower surface of the nanopore layer 102 at the center of the substrate 102, and a nanopore 120 is formed penetrating the nanopore layer 102 which is exposed by the opening.

However, in the case of the nanopore device 300 shown in FIG. 6, the porous material layer 107 is formed in the nanochannel 110 instead of the gel-type filler 115. The porous material layer 107 may be formed of, for example, a porous zeolite or a porous anodized aluminum oxide (AAO). Since target biomolecules may move through the plurality of pores of the porous material layer 107 formed of the material above, the porous material layer 107 may serve as the gel-type filler 115. An inlet 130 may be formed on the cover layer 106 to expose the porous material layer 107. Although two inlets 130 are shown in FIG. 6, only one inlet 130 may be formed. The target biomolecules provided through the inlet 130 translocate through the plurality of pores in the porous material layer 107, and move to the nanopore 120.

FIG. 6 illustrates an example of the porous material layer 107 formed in the nanochannel 110 to be perpendicular to the nanopore 120. However, the porous material layer 107 may be also formed in the nanochannel 110 of the nanopore device 100 shown in FIG. 5, instead of the gel-type filler 115.

As described above, according to the one or more of the above embodiments of the present invention, examples are explained and drawings are described in order to help understanding of a nanopore device, a method of fabricating the same, and a nucleic acid detection apparatus including the same. However, it should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A nanopore device comprising:
   a nanopore;
   a nanochannel connected to the nanopore and having a channel diameter larger than the nanopore; and
   a filler disposed in the nanochannel,
   wherein the filler is a gel or porous material that reduces translocation speed of a biomolecule through the nanochannel as compared to the translocation speed of a biomolecule through the nanochannel in the absence of the filler when the nanochannel contains an electrically conductive solution.

2. The nanopore device of claim 1, wherein the filler is at least one of a silica gel, an agarose gel, and a poly acrylamide gel.

3. The nanopore device of claim 1, wherein the filler comprises at least one of a porous zeolite and a porous anodized aluminum oxide.

4. The nanopore device of claim 1, wherein the nanochannel and the nanopore extend along a common axis so that target biomolecules move in the nanochannel and translocate in the nanopore in a common direction.

5. The nanopore device of claim 4, wherein the nanopore device further comprises:
   a substrate;
   a nanopore layer disposed on the substrate and comprising the nanopore; and
   a nanochannel layer disposed on the nanopore layer and comprising the nanochannel.

6. The nanopore device of claim 5, further comprising an opening in the substrate exposing a part of a lower surface of the nanopore layer, wherein the nanopore is located in a region of the nanopore layer exposed by the opening.

7. The nanopore device of claim 6, wherein the nanochannel extends perpendicular to the nanochannel layer.

8. The nanopore device of claim 6, wherein the opening has a conical surface which becomes broader toward an entrance of the opening.

9. The nanopore device of claim 1, wherein the nanopore and the nanochannel extend perpendicular to each other so that target biomolecules in the nanochannel move in a direction perpendicular to a translocating direction of the target biomolecules in the nanopore.

10. The nanopore device of claim 9, further comprising an inlet connected to the nanochannel, wherein a sample enters into the nanochannel through the inlet.

11. The nanopore device of claim 10, wherein the inlet is placed on an upper surface of each end of the nanochannel, and the nanopore is centrally located on a lower surface of the nanochannel.

12. The nanopore device of claim 10, wherein the inlet is located in an upper area at a first end of the nanochannel, and the nanopore is located in a lower area at a second end of the nanochannel which is located at an opposite side of the first end of the nanochannel.

13. The nanopore device of claim 10, further comprising:
   a substrate;
   a nanopore layer disposed on the substrate and comprising the nanopore;
   a nanochannel layer disposed on the nanopore layer and comprising the nanochannel; and
   a cover layer disposed on the nanochannel layer and comprising the inlet.

14. The nanopore device of claim 13, further comprising an opening in the substrate exposing a part of a lower surface of the nanopore layer, wherein the nanopore is located in a partial region of the nanopore layer exposed by the opening.

15. The nanopore device of claim 13, wherein the nanochannel is disposed between the nanopore layer and the cover layer.

16. The nanopore device of claim 13, wherein the inlet is located in a partial region of the cover layer corresponding to the nanochannel.

17. The nanopore device of claim 14, wherein the opening has a conical surface which becomes broader toward an entrance of the opening.

18. A nucleic acid detection apparatus comprising:
the nanopore device according to claim 1;
a reservoir for containing a sample; and
a power supply configured to generate an electric field around the nanopore in order to move target biomolecules in the sample.

19. A method of fabricating a nanopore device, comprising:
forming a nanopore layer on an upper surface of a substrate;
forming and patterning a mask on a lower surface of the substrate;
forming a nanochannel layer on the nanopore layer;
forming an opening in the substrate by etching the lower surface of the substrate until a lower surface of the nanopore layer is partially exposed;
forming a nanochannel by partially removing the nanochannel layer until an upper surface of the nanopore layer is partially exposed;
forming a nanopore which penetrates the nanopore layer by puncturing a partial region of the nanopore layer where both upper and lower surfaces are exposed; and
introducing a filler into at least a portion of the nanochannel.

20. The method of claim 19, wherein the filler is at least one of a silica gel, an agarose gel, and a poly acrylamide gel.

21. The method of claim 19, wherein the filler is a porous material layer comprising at least one of a porous zeolite and a porous anodized aluminum oxide.

22. The method of claim 19, wherein the nanochannel and the nanopore are formed along a common axis so that target biomolecules move in the nanochannel and translocate in the nanopore in a common direction.

23. The method of claim 19 further comprising forming a cover layer on the nanochannel layer in order to cover the nanochannel and the nanopore.

24. The method of claim 23 further comprising forming an inlet by penetrating a partial region of the cover layer corresponding to the nanochannel.

25. The method of claim 23, wherein the nanopore and the nanochannel are formed perpendicular to each other so that a moving direction of target biomolecules in the nanochannel and a translocating direction of the target biomolecules in the nanopore are perpendicular to each other.

26. The method of claim 19, wherein the opening has a conical surface which becomes broader toward an entrance of the opening.

* * * * *